US012036039B2

United States Patent
Levendowski et al.

(10) Patent No.: US 12,036,039 B2
(45) Date of Patent: *Jul. 16, 2024

(54) SYSTEMS AND METHODS FOR CONTROLLING POSITION

(71) Applicant: Advanced Brain Monitoring, Inc., Carlsbad, CA (US)

(72) Inventors: Daniel J. Levendowski, Carlsbad, CA (US); Timothy Zavora, Reno, NV (US); Philip R. Westbrook, Fallbrook, CA (US); Mirko Mitrovic, Belgrade (RS); Bratislav Veljkovic, Belgrade (RS); Christine Berka, Carlsbad, CA (US); Jonny Trejo, Encinitas, CA (US)

(73) Assignee: ADVANCED BRAIN MONITORING, INC., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/105,120

(22) Filed: Feb. 2, 2023

(65) Prior Publication Data
US 2023/0277127 A1    Sep. 7, 2023

Related U.S. Application Data

(63) Continuation of application No. 16/866,143, filed on May 4, 2020, now Pat. No. 11,571,166, which is a
(Continued)

(51) Int. Cl.
*A61B 5/00*    (2006.01)
*A61B 5/103*   (2006.01)
(Continued)

(52) U.S. Cl.
CPC .............. *A61B 5/486* (2013.01); *A61B 5/103* (2013.01); *A61B 5/11* (2013.01); *A61B 5/1116* (2013.01);
(Continued)

(58) Field of Classification Search
CPC . A61F 5/56; A61M 21/00; A61M 2021/0005; A61M 2021/0022;
(Continued)

(56) References Cited

U.S. PATENT DOCUMENTS

| 4,220,142 A | 9/1980 | Rosen et al. |
| 4,788,533 A | 11/1988 | Mequignon |

(Continued)

FOREIGN PATENT DOCUMENTS

| AU | 768822 B2 | 1/2004 |
| CN | 101053538 A | 10/2007 |

(Continued)

OTHER PUBLICATIONS

Sasse, S.A., et al., Timing of Changes in Oxyhemoglobin Saturation Resulting from Breath Holding. Sleep Medicine, 2006. 7 (S2): p. S46-7.

(Continued)

*Primary Examiner* — Keri J Nelson
(74) *Attorney, Agent, or Firm* — Procopio, Cory, Hargreaves & Savitch LLP

(57) ABSTRACT

Systems and methods for assessing compliance with position therapy. In an embodiment, position therapy is provided to a user while the user is wearing a position therapy device. The position therapy comprises, by the device, collecting positional data, determining positions of the user over a time period based on the positional data, and, when it is determined that the user is in a target position, providing feedback to the user to influence the user to change to a non-target position. In addition, the device stores a duration of use in its memory. The duration of use indicates a duration that the user has used the wearable position therapy device in each of one or more positions. An assessment of the user's (Continued)

compliance with the position therapy is then provided based, at least in part, on the duration of use.

20 Claims, 9 Drawing Sheets

Related U.S. Application Data continuation of application No. 15/825,772, filed on Nov. 29, 2017, now Pat. No. 10,638,973, which is a continuation of application No. 14/313,213, filed on Jun. 24, 2014, now Pat. No. 9,855,006, which is a continuation of application No. 12/794,498, filed on Jun. 4, 2010, now Pat. No. 8,783,264.

(60) Provisional application No. 61/184,631, filed on Jun. 5, 2009.

(51) Int. Cl.
    *A61B 5/11*         (2006.01)
    *A61B 5/113*       (2006.01)
    *A61B 7/00*        (2006.01)
    *A61B 7/04*        (2006.01)
    *A61F 5/56*        (2006.01)
    *A61M 21/02*      (2006.01)
    *A61M 21/00*      (2006.01)
    *A61N 1/36*        (2006.01)
    *A61N 5/06*        (2006.01)

(52) U.S. Cl.
CPC .......... *A61B 5/4806* (2013.01); *A61B 5/4818* (2013.01); *A61B 5/6822* (2013.01); *A61B 5/6823* (2013.01); *A61B 5/7282* (2013.01); *A61B 5/7405* (2013.01); *A61B 7/003* (2013.01); *A61B 7/04* (2013.01); *A61F 5/56* (2013.01); *A61M 21/02* (2013.01); *A61B 5/113* (2013.01); *A61B 5/4809* (2013.01); *A61B 5/4833* (2013.01); *A61B 5/6819* (2013.01); *A61B 5/6831* (2013.01); *A61M 2021/0022* (2013.01); *A61M 2021/0027* (2013.01); *A61M 2021/0044* (2013.01); *A61M 2021/0083* (2013.01); *A61M 2205/3375* (2013.01); *A61M 2205/3569* (2013.01); *A61M 2205/3592* (2013.01); *A61M 2205/502* (2013.01); *A61M 2205/581* (2013.01); *A61M 2205/583* (2013.01); *A61M 2205/8206* (2013.01); *A61M 2209/088* (2013.01); *A61M 2230/63* (2013.01); *A61N 1/3601* (2013.01); *A61N 1/36014* (2013.01); *A61N 1/36031* (2017.08); *A61N 2005/0653* (2013.01)

(58) Field of Classification Search
CPC .. A61M 2021/0027; A61M 2021/0044; A61M 2021/0083; A61M 2205/3375; A61M 2205/3569; A61M 2205/3592; A61M 2205/502; A61M 2205/581; A61M 2205/583; A61M 2205/8206; A61M 2209/088; A61B 5/103; A61B 5/11; A61B 5/1116; A61B 5/4806; A61B 5/4809; A61B 5/4815; A61B 5/4818
See application file for complete search history.

(56) References Cited

U.S. PATENT DOCUMENTS

| | | |
|---|---|---|
| 4,802,485 A | 2/1989 | Bowers et al. |
| 4,830,008 A | 5/1989 | Meer |
| 4,848,360 A | 7/1989 | Palsgard et al. |
| 5,081,447 A | 1/1992 | Echols |
| 5,265,624 A | 11/1993 | Bowman |
| 5,381,801 A | 1/1995 | McShane et al. |
| 5,447,161 A | 9/1995 | Blazek et al. |
| 6,057,767 A | 5/2000 | Barnoach |
| 6,544,199 B1 | 4/2003 | Morris |
| 6,600,949 B1 | 7/2003 | Turcott |
| 6,641,571 B2 | 11/2003 | Redmond et al. |
| 6,811,538 B2 | 11/2004 | Westbrook et al. |
| 6,935,335 B1 | 8/2005 | Lehrman |
| 6,970,792 B1 | 11/2005 | Diab |
| 7,081,095 B2 | 7/2006 | Lynn et al. |
| 7,117,028 B2 | 10/2006 | Bardy |
| 7,118,534 B2 | 10/2006 | Ward et al. |
| 7,311,666 B2 | 12/2007 | Stupp et al. |
| 7,599,892 B1 | 10/2009 | Berger |
| 7,691,067 B2 | 4/2010 | Westbrook et al. |
| 7,717,848 B2 | 5/2010 | Heruth et al. |
| 8,783,264 B2 | 7/2014 | Levendowski et al. |
| 9,198,615 B2 | 12/2015 | Levendowski et al. |
| 9,855,006 B2 | 1/2018 | Levendowski et al. |
| 10,638,973 B2 | 5/2020 | Levendowski et al. |
| 11,571,166 B2 * | 2/2023 | Levendowski ...... A61B 5/4818 |
| 2002/0165462 A1 | 11/2002 | Westbrook et al. |
| 2002/0184050 A1 | 12/2002 | Papageorge |
| 2002/0188205 A1 | 12/2002 | Mills |
| 2003/0199945 A1 | 10/2003 | Ciulla |
| 2004/0015337 A1 | 1/2004 | Thomas et al. |
| 2005/0197588 A1 | 9/2005 | Freeberg |
| 2005/0234313 A1 | 10/2005 | Rowlandson et al. |
| 2006/0074334 A1 | 4/2006 | Coyle |
| 2006/0100538 A1 | 5/2006 | Genger et al. |
| 2007/0208269 A1 | 9/2007 | Mumford et al. |
| 2007/0214013 A1 | 9/2007 | Silverman |
| 2007/0282177 A1 | 12/2007 | Pilz |
| 2008/0234598 A1 | 9/2008 | Snyder et al. |
| 2008/0264426 A1 | 10/2008 | Walker |
| 2008/0319277 A1 | 12/2008 | Bradley |
| 2009/0120446 A1 | 5/2009 | Vaska et al. |

FOREIGN PATENT DOCUMENTS

| | | |
|---|---|---|
| CN | 101340869 A | 1/2009 |
| EP | 1578251 A | 5/2008 |
| JP | 0349748 H | 3/1991 |
| JP | 07213546 H | 8/1995 |
| JP | 2005185650 A | 7/2005 |
| JP | 2005270627 A | 10/2005 |
| JP | 2005312901 A | 11/2005 |
| JP | 2005318907 A | 11/2005 |
| JP | 2007199025 A | 8/2007 |
| JP | 2007294143 A | 11/2007 |
| JP | 2008011865 A | 1/2008 |
| JP | 2009519802 A | 5/2009 |
| WO | 2002065901 A2 | 8/2002 |
| WO | 2006133548 A1 | 12/2006 |
| WO | 2007072390 A1 | 6/2007 |
| WO | 2007100959 A2 | 9/2007 |
| WO | 2008008915 A2 | 1/2008 |
| WO | 2011139141 A1 | 11/2011 |

OTHER PUBLICATIONS

Standards and Practice Committee of the American Sleep Disorders Association. ASDA Standards of Practice, Practice Parameters for the Use of Portable Recording in the Assessment of Obstructive Sleep Apnea . . . Sleep, 1994 17(4), p. 372-377.
Warner, David S. et al., Obstructive Sleep Apnea of Obese Adults, Anesthesiology, vol. 110, No. 4, Apr. 2009, pp. 908-921.
Westbrook P, et al. Predicting Effective Continuous Positive Airway Pressure (CPAP) based on Laboratory Titration and Auto-titrating CPAP, 8th World Congress on OSA. Sleep Medicine. vol. 7, Suppl. 2. 2006. 2 pages.
Westbrook P, et al. Predicting Treatment Outcomes for Oral Appliance Therapy for Sleep Apnea using Pre-treatment in-home Sleep

(56) References Cited

OTHER PUBLICATIONS

Studies, 8th World Congress on OSA. Sleep Medicine. vol. 7, Suppl. 2. 2006. p. 1-2.
Westbrook, P., et al. Validation of an Apnea Risk Evaluation Questionnaire. in American Thoracic Society International Conference. 2005. San Diego, CA. 2 pages.
Westbrook, P., et al., Description and Validation of the Apnea Risk Evaluation System: A Novel Method to Diagnose Sleep Apnea-Hypopnea in the Home. Chest, 2005. 128(4): p. 2166-75.
Wilson, Kerryn et al., Can Assessment for Obstructive Sleep Apnea Help Predict Postadenotonsillectomy Respiratory Complications, Anesthesiology, vol. 96, No. 2, Feb. 2002, pp. 313-322.
Young, T., et al., Epidemiology of Obstructive Sleep Apnea: A Population Health Perspective. Am J Respir Crit Care Med, 2002. 165(9): p. 1217-39.
Attachment A to Email From Michael Gorman to Dan Levendowski, Entitled "Some stuff", sent Mar. 23, 2012.
Attachment B to Email From Michael Gorman to Dan Levendowski, Entitled "Some stuff", sent Mar. 23, 2012.
Attachment C to Email From Michael Gorman to Dan Levendowski, Entitled "Some stuff", sent Mar. 23, 2012.
Bignold, "A Novel Positional Therapy Device for Supine Related Obstructive Sleep Apnoea" 2008) Adelaide Institute for Sleep Health.
Email From Michael Gorman to Dan Levendowski, Entitled "Some stuff", sent Mar. 23, 2012.
Gorman. "S27/28 Notice for 2010256401." Nov. 14, 2014. 48 pages.
Jordan et al., "Ventilatory Response to Brief Arousal From Non-Rapid Eye Movement Sleep Is Greater in Men Than in Women" 2003), Adelaide Institute for Sleep Health.
Alemohammad, M., Z Khan, M Sanatkar, S Mirkhani, Ghorbandaie-Poure I., Pressure measurements during cardiac surgery—internal jugular vs. central venous. Middle East J Anestesiol. 2005; 18(2):357-65.
Cox P, Johnson JO, Tobias JD. Measurement of central venous pressure from a peripheral intravenous catheter in the lower extremity. South Med J. Jul. 2005;98(7):698-702.
Examination Report dated Feb. 11, 2019 for corresponding AU Patent Application No. 2018200573, in 7 pages.
Examination Report dated Jun. 13, 2019 for related AU Patent Application No. 2018200573, in 5 pages.
Extended European Search Report for related EP Patent Application No. 19156894.8, dated Aug. 2, 2019, in 7 pages.
Farre R, Montserrat JM, Navajas D. Noninvasive monitoring of respiratory mechanics during sleep. Eur Respir J. Dec. 2004;24(6):1052-60.
Foo J, Wilson S, Bradley A, Williams G, Harris M, Cooper D. Use of pulse transit time to distinguish respiratory events from tidal breathing in sleeping children. Chest 2005; 128; 3013-3019.
Gisolf J, Van Lieshout J, Van Heusden K, Pott F, Stok W, Karemaker J. Human cerebral venous outflow pathway depends on posture and central venous pressure. J Physiol 560.1 (2004) 317-327.
Haba-Rubio J, Darbellay G, Herrmann FR, Frey JG, Fernandes A, Vesin JM, Thiran JP, Tschopp JM. Obstructive sleep apnea syndrome: effect of respiratory events and arousal on pulse wave amplitude measured by photoplethysmography in NREM sleep. Sleep Breath (2005) 9: 73-81.
Hofsoy, D A, 'A One-Sensor System for Home Diagnosis and Therapy of Snoring and Sleep Apnea', Master Thesis Abstract [retrieved from internet on Feb. 4, 2019]. <URL: https://brage.bibsys.no/xmlui/handle/11250/2368993> published 2007.
Waldemar Carlo et al., Alae nasi activation (nasal flaring) decreases nasal resistance in preterm infants. Pediatrics vol. 72, Issue 3, pp. 338-343.
International Search Report/Written Opinion issued in PCTUS2007071242 dated Mar. 13, 2008, 11 pages.
Johansson A, Oberg PA. Estimation of respiratory volumes from the photoplethysmographic signal. Part 2: A model study. Med Biol Eng Comput. Jan. 1999;37(1):48-53.
Johansson A, Oberg PA. Estimation of respiratory volumes from the photoplethysmographic signal. Part I: Experimental results. Med Biol Eng Comput. Jan. 1999;37(1):42-7.
Johansson A, Stromberg T. Influence of tidal volume and thoracoabdominal separation on the respiratory induced variation of the photoplethysmogram. J Clin Monit Comput. 2000;16(8):575-81.
Johansson A. Neural network for photoplethysmographic respiratory rate monitoring. Med Biol Eng Comput. May 2003;41(3):242-8.
Kushida C, Giocomini A, Lee M, Guilleminault C, Dement W. Technical protocol for the use of esophageal manometry in the diagnosis of sleep-related breathing disorders. Sleep Med 3(2002) 163-173.
Leonard P, Grubb NR, Addison PS, Clifton D, Watson JN. An algorithm for the detection of individual breaths from the pulse oximeter waveform. J Clin Monit Comput. Dec. 2004;18(5-6):309-12.
Lofsky, Ann, Sleep apnea and narcotic postoperative pain medication: a morbidity and mortality risk. Anesthesia Patient Safety Foundation Newsletter. Summer 2002:24-25.
Magder S. How to use central venous pressure measurements. Curr Opin Crit Care. Jun. 2005;11(3):264-70.
Mannheimer P, O'Neil M, Konecny E. The influence of large subcutaneous blood vessels on pulse oximetry. J Clin Monitor Comput 18:179-188, 2004.
Nakajima K, Tamura T, Miike H. Monitoring the heart and respiratory rates by photoplethysmography using a digital filtering technique. Med Enq Phys 1996 1 8(5) 365-372.
Neligan, Patrick J. et al., Continuous Positive Airway Pressure via the Boussignac System Immediately after Extubation Improves Lung Function in Morbidly Obese Patients with Obstructive Sleep Apnea Undergoing Laparoscopic Bariactric Surgery, Anesthesiology, vol. 110, No. 4, Apr. 2009, pp. 878-884.
NightBalance B.V. "Statement of Grounds and Particulars." Submitted to the AU Patent Office on Feb. 13, 2015 in relation to Australian Patent Application No. 2010256401, 11 pages.
Nilsson et al., Monitoring of respiratory rate in postoperative care using a new photoplethysmographic technique. J Clin Monit Comput. 2000; 16(4):309-15.
Notice of Acceptance for related AU Patent Application No. 2018200573, dated Oct. 16, 2019, in 3 pages.
Office Action dated Nov. 1, 2018 for related IN Patent Application No. 2781/MUMNP/2011, in 6 pages.
Pilcher, D., C Scheinkestel, G Snell, A Davey-Quinn, M Bailey, T Williams. High central venous pressure is associated with prolonged mechanical ventilation and increased mortality after lung transplantation. J Thorac Cardiovasc Surg. 2005;129(4):912-8.
Pitson D, Stradling J. Value of beat-to-beat blood pressure changes, detected by pulse transit time, in the management of obstructive sleep apnea/hypopnea syndrome. Eur Respir J 1998:12:685-692.
Shepard JW Jr, Pevernagie DA, Stanson AW, Daniels BK, Sheedy PF. Effects of changes in central venous pressure on upper airway size in patients with obstructive sleep apnea. Am J Respir Crit Care Med. Jan. 1996;153 (1):250-4.
Teng XF, Zhang YT. The effect of contacting force on photoplethysmographic signals. Physiol Meas. Oct. 2004;25(5):1323-35.
A Report by the American Society of Anesthesiologists Task Force on Perioperative Management of Patients with Obstructive Sleep Apnea, Practice Guidelines for the Perioperative Management of Patients with Obstructive Sleep Apnea. Anesthesiology, 2006. 104(5): p. 1081-1093.
Argod J, Pepin J, Smith R, Levy P. Comparison of Esophageal Pressure with Pulse Transit Time as a measure of respiratory effort for scoring obstructive nonapneic respiratory events. Am J Respir Crit Care Med vol. 162 (2000) 87-93.
Aurell, J. and D. Elmqvist, Sleep in the surgical intensive care unit: continuous polygraphic recording of sleep in nine patients receiving postoperative care. Sr Med J (Clin Res Ed), 1985. 290(6474): p. 1029-32.
Benumof, J.L., Obesity, sleep apnea, the airway, and anesthesia. Current Opinion in Anaesthesiology, 2004. 17(1): p. 21-30.

(56) References Cited

OTHER PUBLICATIONS

Benumof. J.L., Obstructive sleep apnea in the adult obese patient: implications for airway management. Anesthesiology Clinics of North Arnerica, 2002. 20(4): p. 789-811.

Brown, K.: Intermittent Hypoxia and the Practice of Anesthesia. Anesthesiology. 2009 110(4). p. 922-7.

Cannesson M, Besnard C, Durand PG, Bohe J, Jacques D. Relation between respiratory variations in pulse oximetry plethysmographic waveform amplitude and arterial pulse pressure in ventilated patients. Crit Care. Oct. 5, 2005;9(5): R562-8. Epub Aug. 23, 2005.

Catcheside et al., Noninvasive Cardiovascular Markers of Acoustically Induced Arousal from Non-Rapid eye-movement Sleep, (2002) Sleep vol. 25 No. 7.

Catley, DM., et al., Pronounced, episodic oxygen desaturation in the postoperative period: its association with ventilatory pattern and analgesic regimen. Anesthesiology, 1985. 63(1): p. 20-8.

Chung et al., A Systemic Review of Obstructive Sleep Apnea and Its Implications for Anesthesiologists, Ambulatory Anesthesiology, vol. 107, No. 5, Nov. 2008, pp. 1543-1563.

Cronin, A., et al., Opioid inhibition of rapid eye movement sleep by a specific mu receptor agonist. Br J Anaesth, 1995. 74(2): p. 188-92.

Den Herder, Cindy et al., Risks of General Anaesthesia in People with Obstructive Sleep Apnoea, BMJ, vol. 329, Oct. 23, 2004, pp. 955-959 and 1 cover sheet.

Deutscher, R., et al., OSA protocol promotes safer care. Anesthesia Patient Safety Foundation Newsletter 2002-2003: p. 58-60.

Ellis, B.W. and H.A. Dudley, Some aspects of sleep research in surgical stress. J Psychosom Res, 1976. 20(4): p. 303-8.

Extended European Search Report dated Jun. 17, 2013 for related EP Application No. 10784198.3 in 7 pages.

Finkel, K., et al., Obstructive Sleep Apnea: The Silent Pandemic. in ASA Annual Meeting. 2006. Chicago, IL.: 1 page.

Finkel, K., et al., The Silent Perioperative Pandemic. Sleep Review, 2006. 7(4): p. 56-60.

Foo JY, Wilson SJ. Estimation of breathing interval from the photoplethysmographic signals in children. Physiol Meas. Dec. 2005;26(6):1049-58. Epub Oct. 31, 2005.

Gali, B.: Identification of Patients at Risk for Postoperative Respiratory Complications Using a Preoperative Obstructive Sleep Apnea Screening Tool and Postanesthesia Care Assessment. Anesthesiology. 2009 110(4). p. 869-77.

Gali, Bhargavi et al., Management Plan to Reduce Risks in Perioperative Care of Patients with Presumed Obstructive Sleep Apnea Syndrome, JCSM Journal of Clinical Sleep Medicine, vol. 3, No. 6, 2007, pp. 582-588.

Gentil, B., et al., Enhancement of postoperative desaturation in heavy snorers. Anesth Analg, 1995. 81(2): p. 389-92.

Gupta, R., et al., Postoperative complications in patients with obstructive sleep apnea syndrome undergoing hip or knee replacement: a case-control study. Mayo Clinic Proceedings, 2001. 76: p. 897-905.

International Search Report and Written Opinion as issued in International Patent Application No. PCT/US2010/037507 dated Feb. 21, 2011, 8 pages.

International Search Report and Written Opinion for PCT/US2010/027679 dated Oct. 19, 2010, 11 pages.

Kaw, R., et al., Unrecognized Sleep Apnea in the Surgical Patient: Implications for the Perioperative Setting. Chest, 2006. 129(1): p. 198-205.

Keifer, J., et al.. Sleep Disruption and Increased Apneas after Pontine Microinjection of Morphine. Anesthesiology, 1992. 77(5): p. 973-82.

Kheterpal, Sachin et al., Prediction and Outcomes of Impossible Mask Ventilation, Anesthesiology, vol. 110, No. 4, Apr. 2009, pp. 891-897.

Knill, R., et al., Anesthesia with Abdominal Surgery Leads to intense REM Sleep during the First Postoperative Week. Anesthesiology, 1990. 73(1): p. 52-61.

Lickteig, Carla et al., Risks of OSA and Anesthesia, Sleep Review, Jan./Feb. 2003, 5 pages.

Loadsman, J. and D. Hillivian, Anaesthesia and sleep apnoea. British Journal of Anaesthesia, 2001. 86(2): p. 254-266.

Nilsson et al., Age and gender do not influence the ability to detect respiration by photoplethysmography. J Clin Monit Comput. Dec. 2006; 20(6), pp. 431-436. Epub Oct. 11, 2006.

Nilsson et al., Macrocirculation is not the sole determinant of respiratory induced variations in the reflection mode photoplethysmographic signal. Physiol Meas. Nov. 2003; 24(4):925-37.

Nilsson et al., Respiration can be monitored by photoplethysmography with high sensitivity and specificity regardless of anaesthesia and ventilatory mode. Acta Anaesthesiol Scand. Sep. 2005; 49(8): 1157-62.

Nilsson et al., Respiratory variations in the reflection mode photoplethysmographic signal. Relationships to peripheral venous pressure. Med Biol Comput. May 2003;41(3):249-54.

Office Action and Search Report (with English translation) for related CN Patent Application No. 201080022673.7, dated Aug. 16, 2013, in 14 pages.

Oliver, Z. and V. Hoffstein, Predicting effective continuous positive airway pressure. Chest, 2000. 117(4): p. 1061-4.

Orr, W.C. and M.L. Stahl, Sleep disturbances after open heart surgery. Am J Cardiol, 1977. 39(2): p. 196-201.

Pembrook, Linda. High Risk for Sleep Apnear Found in Pain Patients on Opioids, Issue: Jun. 2006, vol. 32:06, 3 pages.

Ramachandran et al., A Meta-analysis of Clinical Screening Tests for Obstructive Sleep Apnea, Anesthesiology, Vo. 110., No. 4, Apr. 2009, pp. 928-939.

Reeder, M.K., et al., Late postoperative nocturnal dips in oxygen saturation in patients undergoing major abdominal vascular surgery. Predictive value of pre-operative overnight pulse oximetry. Anaesthesia, 1992. 47(2): p. 110-5.

Reeder, M.K., et al., Postoperative hypoxaemia after major abdominal vascular surgery. Sr J Anaesth, 1992. 68(1): p. 23-6.

Reeder, M.K., et al., Postoperative obstructive sleep apnoea. Haemodynamic effects of treatment with nasal CPAP. Anaesthesia, 1991. 46(10): p. 849-53.

Rejection dated Jan. 21, 2014 in related JP Patent Application No. 2012-514198 in 8 pages.

Remmers, J.E., et al. , Pathogenesis of upper airway occlusion during sleep. J Appl Physiol.: Respirat. Environ. Exercise Physiol., 1978. 44(6): p. 931-8.

Rock, P. and A. Passannante, Preoperative assessment pulmonary. Anesthesiology Clinics of North America, 2004. 22(1): p. 77-91.

Rosenberg, J. and H. Kehlet, Postoperative episodic oxygen desaturation in the sleep apnoea syndrome. Acta Anaesthesiol Scand, 1991. 35(4): p. 368-9.

Rosenberg, J., et al., Circadian variation in unexpected postoperative death. Br J Surg, 1992. 79(12): p. 1300-2.

Rosenberg, J., et al., Late postoperative nocturnal episodic hypoxaemia and associated sleep pattern. Br J Anaesth, 1994. 72(2): p. 145-50.

Rosenberg-Adamsen, et al., Postoperative sleep disturbances: mechanisms and clinical implications. Br J Anaesth, 1996. 76(4): p. 552-9.

Sabers, C., et al.: The diagnosis of obstructive sleep apnea as a risk factor for unanticipated admissions in outpatient surgery. Anesth Analg. May 2003;96(5):1328-35.

\* cited by examiner

SYSTEMS AND METHODS FOR CONTROLLING POSITION

CROSS-REFERENCE TO RELATED APPLICATIONS

This application is a continuation of U.S. patent application Ser. No. 16/866,143, filed on May 4, 2020, which is a continuation of U.S. patent application Ser. No. 15/825,772, filed on Nov. 29, 2017, which is a continuation of U.S. patent application Ser. No. 14/313,213, filed on Jun. 24, 2014, now U.S. Pat. No. 9,855,006, which is a continuation of U.S. patent application Ser. No. 12/794,498, filed on Jun. 4, 2010, now U.S. Pat. No. 8,783,264, which claims the benefit of U.S. Provisional Patent App. No. 61/184,631, filed on Jun. 5, 2009, all of which are hereby incorporated herein by reference in their entireties.

BACKGROUND

Field of the Invention

The present invention generally relates to the field of treating sleep disorders and more specifically to systems and methods using position therapy (PDT) to treat sleep disorders.

Description of Related Art

Sleep disordered breathing which results in the diagnosis of Obstructive Sleep Apnea ("OSA") occurs as a result of a partial or complete collapse of the upper airway during sleep. Snoring is the first indication of an airway susceptible to collapse and can lead to inspiratory flow limitation. Greater obstruction resulting in a partial collapse of the airway causes hypopneas and recognizable changes in tidal volume. Full collapse results in a cessation in breathing, events commonly referred to as apneas. The apnea/hypopnea index (AHI) is the measure used to define OSA severity and is based on the total number of sleep disordered breathing events per hour of sleep.

When a patient with OSA is in the supine position, gravity increases the susceptibility of the airway to partial or full collapse during sleep. The most frequently cited effect of gravity on the soft tissue of the pharynx is tendency of the tongue to fall back against the palate causing the narrowing of an already compromised airway. A susceptible airway, by way of example, may result in loud snoring in the supine position and limited or no snoring the non-supine position. A more compromised airway may exhibit loud snoring in the non-supine position and repeated hypopneas (partial collapse) or apneas (full collapse) in the supine position. This pattern is typically associated with patients with 'positional' sleep disordered breathing. In patients with severely compromised airways, known as 'non-positional' OSA, the pharynx may partially collapse during non-supine sleep and fully collapses in the supine position. The influence of gravity during supine sleep contributes to a reduction in lung volume and oxygen stores and contributes to increased levels of oxygen desaturation during obstructive breathing.

Evidence suggest that patients with positional and non-positional OSA form two distinct but overlapping etiologies in which airway length and craniofacial features influence genioglossal responsiveness to negative pressure pulses in the lateral position. Estimate of the prevalence of positional OSA (i.e., the supine AHI is at least two times greater than the non-supine AHI) among all those diagnosed with OSA range from 55 to 65%), and after excluding those who sleep almost exclusively on their back (e.g., >95% of the night), over 50% of patients diagnosed with sleep could reduce their AHI by at least 50% and/or into a normal range by avoiding sleep in the supine position. Studies have shown that position therapy can contribute to a significant drop in blood pressure in patients with Obstructive Sleep Apnea (OSA) because supine sleep increases the severity of OSA. Position therapy can be combined with other therapies to enhance outcomes in the treatment of sleep disordered breathing. Several investigators have demonstrated nasal continuous positive airway pressure (CPAP) pressures can be reduced if patients sleep lateral instead of supine and increased CPAP compliance has been associated with lower pressures.

A plethora of shirts, vests, belts, pillows and other inventions have attempted to address the need for positional therapy to reduce the severity of snoring or sleep apnea by using mechanical means that essentially makes it uncomfortable for a user to sleep supine. Some examples of these devices include a knapsack stuffed with Styrofoam to provide a bulky alternative to tennis balls, which makes it impossible to sleep supine. At least one study has demonstrated that this type of position restriction provides limited to no clinical efficacy due to non-compliance. The greatest limitation of these approaches is that the therapy is initiated prior to the patient falling asleep. As shown with CPAP therapy, patients are much more tolerant of therapy if it is initiated after the patients have fallen asleep.

The number of electronic devices invented to limit supine sleep is substantially less. One device, described in U.S. Pat. No. 5,081,447, employs the use of two gravity position sensors and an audio alarm to trigger the user to change position. One of the limitations of this approach is a bed-partner of the user would also be awakened each time the alarm is triggered. An alternative approach, described in U.S. Pat. No. 5,381,801, limits supine sleep by applying electromechanical vibration using motors inserted into pockets of a belt worn by a user. Application of the tactile stimulus is dependent on the closing of an electronic switch within the pocket of the belt that is triggered by contact with the underlying surface of the sleeper.

Positional therapy holds the potential to provide important therapeutic benefit for a number of medical conditions. For example, over 63% of patients with acute ischemic stroke sleep the entire night in the supine position. Sleep in the supine position also increases the severity of Cheyne-Stokes i.e., respiration i.e., central sleep apnea. Avoiding supine sleep during the second and third trimesters of pregnancy would reduce pressure on a vena cava vein and improve blood flow to the fetus. An adjustment in the application of position feedback would assist patients recovering from hip surgery avoid sleep in the non-supine position. The measurement of and feedback related to the position of the elements of the body (e.g., arm, leg, hand, wrist, ankle, knee, etc.) could be useful in injury rehabilitation or in training or performance which requires the user to find or maintain a specific position/posture. Thus, the potential benefit of positional therapy is clear, but conventional systems and methods to affect or influence sleep position have been largely ineffective.

SUMMARY

Systems and methods for controlling the position of a user of a wearable positional therapy device are provided. In one embodiment, the wearable position therapy device is configured to monitor and store physiological signals that can be used to assess sleep quality and sleeping position of a user as well as during other activities. The device can be configured to be worn around the head, the neck, or body of the user and/or can comprise of more than one unit that are connected wirelessly to share information. The device can be configured to provide feedback to a user if the user is sleeping or is positioned in a target position to induce the user to change positions. For example, the device can be configured to limit the amount of time that the user spends sleeping in a supine position for users for whom it is not recommended to sleep in a supine position, such as OSA patients and users who are pregnant. The feedback can be provided by one or more haptic motors that can be configured to provide various levels of feedback and the level of feedback can be customized based on the user's reaction to the feedback.

In an embodiment, a wearable position therapy device for influencing the position of a user is provided. The device includes a position detector configured to generate positional signal data that can be used to determine a position of the user, a haptic feedback device configured to generate tactile feedback to the user of the device, and a microcontroller. The microcontroller is configured to receive and analyze the signal data from the position detector, determine whether the user of the device is in a target position, and generate a control signal to cause the haptic feedback device to provide tactile feedback to the user to induce the user to change to a different, non-target position if the user of the device is in a target position. In an embodiment, the position therapy device can be configured to influence a sleeping position of a user and can be worn while the user sleeps. The target position can be a target sleep position, and the microcontroller can be configured to generate a control signal to cause the haptic feedback device to provide tactile feedback to the user to induce the user to change to a different, non-target sleep position if the user of the device is in a target sleep position.

In another embodiment, a method for influencing the position of a user using a wearable position therapy device is provided. The method includes applying the position therapy devices to the head, neck, body, torso, hand, wrist or knee of the user, collecting positional signal data to determine a position and manner of the user while the user is wearing the device, determining whether the positional signal data indicates that the user is positioned in a target position, and generating haptic feedback to the user to induce the user to change to a different, non-target position if the user is in the target position. In an embodiment, the method can be used to influence a sleeping position of a user of the wearable position therapy device, and the positional signal data can be used to determine whether the user is in a target sleep position, and to provide haptic feedback to the user if the user is in the target sleep position to influence the user to change to a different, non-target sleep position.

DETAILED DESCRIPTION

Figure 1:
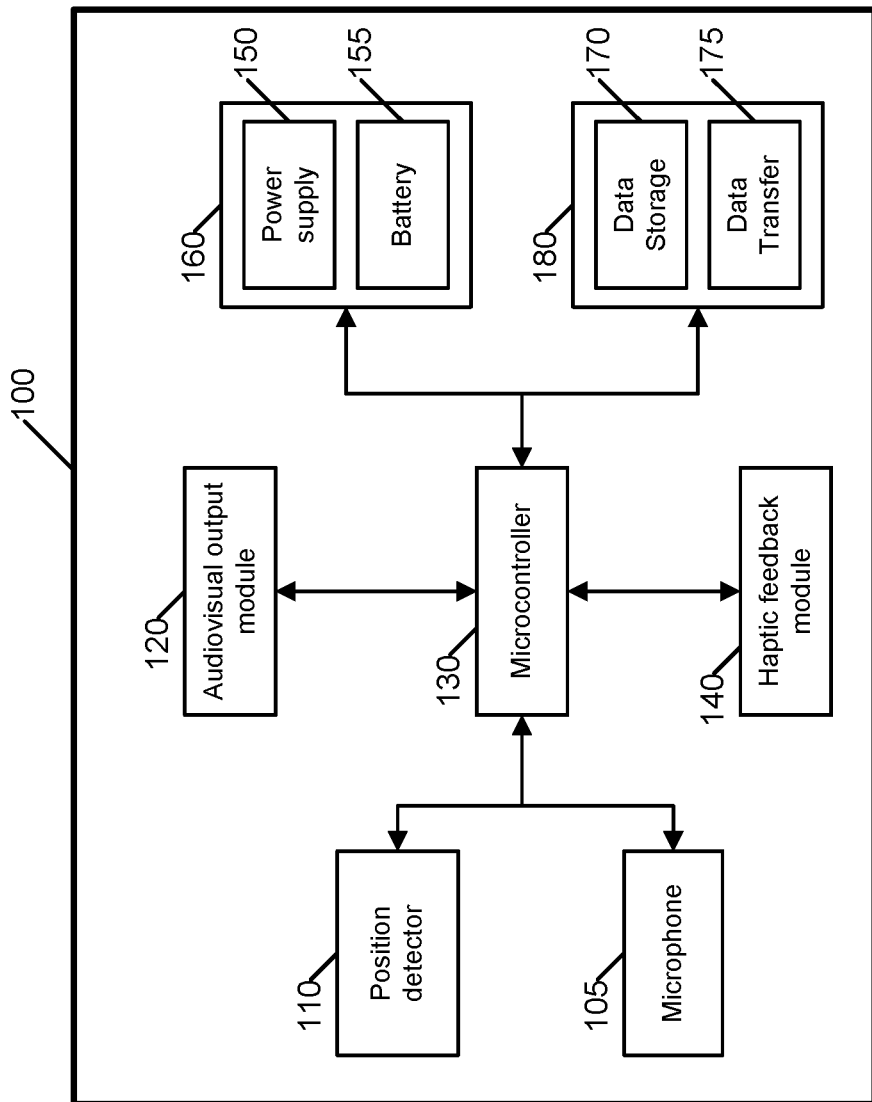
FIG. 1 identifies the primary electronic components and circuits of a position therapy device configure to monitor and reduce sleep in a target position according to an embodiment.

Systems and methods for influence position of a user are provided. Embodiments can be used to control the influence the position of a user's body, and some embodiments can be used to influence a sleeping position of the user. The device can be configured to be worn around the head, the neck, or body of the user. The device can be configured to provide feedback to a user if the user is sleeping or is positioned in a target position to induce the user to change positions. For example, the device can be configured to limit the amount of time that the user spends sleeping in a supine position for users for whom it is not recommended to sleep in a supine position, such as OSA patients and users who are pregnant. The feedback can be provided by one or more haptic motors that can be configured to provide various levels of feedback and the level of feedback can be customized based on the user's reaction to the feedback.

According to one embodiment, a wearable position therapy device is provided that is configured to monitor and store physiological signals that can be used to assess sleep quality and sleeping position of a user. The device can be worn around the head, the neck, or body of the user. The device can be configured to provide haptic feedback to induce the user change sleeping positions if the position therapy device determines that the user is sleeping in a target position. In an embodiment, the form factor of the device is comfortable so as to not disturb the user's ability to sleep while wearing the device. The device is also easy for a user to self-apply. The device can be configured to provide feedback, including haptic feedback, to influence the user's sleep positions. Adaptive feedback routines can be included to minimize the disruption of sleep continuity while reducing the likelihood that the user does not return to the target sleep position. The application of feedback can be provisionally set so the device can worn to first obtain baseline sleep data for comparison to the changes in sleep position after initiation of feedback. The signals recorded during the night(s) can be analyzed to assess parameters useful in assessing treatment compliance and efficacy, such as total sleep time and sleep efficiency, snoring frequency and loudness, and percentage of sleep time by position.

Embodiments of the position therapy device can also be used in applications where the user is not sleeping but it is desirable for the user to avoid specific positions. For example, a pregnant user experiencing pre-eclampsia might be confined to bed rest by a physician and instructed to avoid laying in a supine position when both asleep and awake in order to avoid aggravating the condition.

According to an embodiment, the target position can also be defined as a position that the position therapy device will discourage the user from being in that position. In some embodiments, a set of allowable positions can be defined and if the user moves to a position that is not included in the set of allowable positions that position can be considered a target position, and the position therapy device can be configured to provide feedback to the user to induce the user to change positions to one of the allowed positions. This approach can be useful in teaching or training exercises where the position therapy device can be used to train a user to be in a certain position.

FIG. 1 is a block diagram identifying functional components and circuits of a Position Therapy Device ("PTD") 100 according to an embodiment. The PTD 100 can be configured to be worn on the head, neck, or body of a user. In some embodiments, the PTD 100 can be worn during sleep to influence the position of the user's body. In other embodiments, the PTD 100 can be worn while the user is awake to provide feedback to the user if the user positions his or her body in a predetermined target position to be avoided. In an embodiment, the PTD 100 includes a microcontroller 130, a haptic feedback device 140, power supply 150, battery 155, recharging circuit 160, and position detector 110. FIG. 1 illustrates the various components of the PTD 100 as being in communication with one another. The components can be in communication with one another via a wired or wireless connection.

The position detector 110 is configured to generate signal data that can be analyzed by the PTD 100 to determine the sleeping position of the user. For example, the position detector 110 can be used to determine whether the user is in a supine position. According to an embodiment, the position detector 110 can comprise an accelerometer. According to an alternative embodiment, a pressure switch or sensor can be used instead of an accelerometer. When the PTD 100 is worn on the user's the neck or against the user's back, the pressure switch or sensor can be used to detect when the user is sleeping or laying in a supine position.

According to an embodiment, the PTD 100 can include a microphone 105 that can be configured to capture audio data while the user is sleeping. This audio data can be analyzed by the PTD 100 to detect snoring and/or other audible symptoms that can be causing sleep disruption. Snoring can be an indicator of obstructed breathing, and the PTD 100 can be used in a therapy regime for OSA in which a user is discouraged from sleeping in a supine position. In an example, microphone 105 can be used to capture audio signals to assess snoring magnitude and frequency, which are likely to be position dependent. In a preferred embodiment an acoustic microphone is used to obtain quantified levels of snoring. In an alternative embodiment, a vibration microphone can be used instead of an acoustic microphone. In an embodiment, the PTD 100 can be configured to correlate the audio data captured by microphone 105 with positional data generated by the position detector 110 to determine whether to provide haptic and/or audiovisual feedback to the user to induce the user to shift to a different sleep position. For example, a user having OSA can be induced to sleep in a non-supine position if severe snoring is detected by the PTD 100.

In the embodiment illustrated in FIG. 1, the PTD 100 includes a power component 160 that includes a rechargeable battery 155 and a power supply 150 for receiving power from an external source for recharging battery 155 via recharging circuit 260 and/or powering the PTD 100. The battery 155 allows the PTD 100 to operate without requiring the PTD 100 to be tethered to an external power cord or power supply, which could be inconvenient and uncomfortable for a user of the device. In the preferred embodiment, the battery capacity is sufficient to allow the PTD 100 to acquire data from multiple nights while providing the required haptic feedback to the user.

In one embodiment, battery 155 can be a rechargeable lithium polymer battery. According to other embodiments, battery 155 can be another type of battery, either rechargeable or non-rechargeable, and in some embodiments, battery 155 can be removable and replaceable. According to one embodiment, battery 155 is a rechargeable battery that includes a micro-USB connector that allows battery 155 to be recharged using a standard USB charger that plugs into an electrical outlet or a standard USB host. In an embodiment, the recharging circuit 160 comprises a standard USB wall charger that plugs into a standard wall outlet in order to power the PTD 100 and/or recharge battery 155 using mains power. According to some embodiments, an external power supply can be used to power the device.

The PTD 100 can include a memory 170 for data storage. In an embodiment, the memory 170 can comprise a removable Multimedia Memory card (MMC) or Secure Digital card (SD) car or other types of removable persistent memory. In another embodiment, the memory 170 can comprise a fixed flash chip. According to an embodiment, a data transfer interface 175 is provided. According to an embodiment, the data transfer interface 175 can comprise a micro-USB or similar type of connector that can be used facilitate downloading data from the PTD to an external computer system or web portal, for uploading firmware executable by microcontroller 130 to memory 170, or both. In an embodiment, the data transfer interface 175 can also include a mechanical interface for providing power to the recharging component 160 to recharge the battery 155.

According to an embodiment, most commercially available microcontrollers or microprocessor 130 would be appropriate for the PTD 100. However, in a preferred embodiment, the microcontroller 130 is an inexpensive, small, low-powered chip. The PTD 100 can include firmware executable by the microcontroller 130. The firmware can be stored in data storage 170 or in a flash memory of microcontroller 130. According to some embodiments, the firmware can be updated by downloading new firmware from an external computer system via data transfer interface 175.

According to an embodiment, the firmware can be configured to minimize the power requirements of the microcontroller 130 while the PTD 100 is being used in recording mode to capture data from the position detector 110, the microphone 105, and/or other sensors. The firmware can be configured to analyze data received from the position detector 110, microphone 105, and/or other sensors and to provide feedback to the user of the device via audiovisual output module 120 and/or haptic feedback device 140 for providing tactile feedback to the user of the PTD 100. In an embodiment, the haptic feedback device can comprise one or more haptic motors for providing tactile feedback to the user of the PTD 100. In an embodiment, the PTD 100 can be configured to store various position therapy (PDT) data to the memory 170. The PDT data can include data received from the position detector 110 and/or the microphone 105. The PDT data can include data, such as the sleep position at various times, the changes to the sleep position of the user, sleep state and arousals, snoring data, and/or other data that can be recorded and/or generated by the PDT 100.

In an embodiment, the PTD 100 can be configured to store various position therapy (PDT) data to the memory 170. The PDT data can include data received from the position detector 110 and/or the microphone 105. The PDT data can include data, such as the sleep position at various times, the changes to the sleep position of the user, sleep state and arousals, snoring data, and/or other data that can be recorded and/or generated by the PDT 100.

According to an embodiment, the PTD 100 can be configured to write an action history to the memory 170 to assist customer service support. For example, information regarding when the battery 155 of the PTD 100 has been charged, when the device has been powered on and off, when the device has started and stopped recording sleep assessment data about the user, and other information can be included in the action history that is written to memory 170.

In an embodiment, the data transfer interface comprises a Universal Serial Bus (USB) data transfer chip to facilitate transferring of data captured by the PTD 100 to an external computer system or web portal. In another embodiment, USB transfer capabilities can be incorporated into microcontroller 130.

The memory 170 can be used to store data collected by the PTD 100 while the device is being worn by a user. Alternatively, this information can be stored to the flash of the microcontroller 130. To avoid data loss when saving to flash memory, the firmware can identify when the battery power is low and can conserve power until the data is downloaded.

In an embodiment, to improve the ease and speed of transfer of files from the data storage device, a USB flash drive chip can be included in the PTD 100. In some embodiments, the capability to transfer data via USB or native USB is provided by the microcontroller 130. According to an embodiment, the PTD 100 can be connected to an external computer system via a USB connection, and the PTD 100 can be recognized as a USB Human Interface device, which can allow direct control of the device by the Microsoft Windows operating system and/or by Web-based software.

In an embodiment, the PTD 100 includes one or more haptic motors 140 that can be configured to elicit vibrations in response to control signals from the to provide haptic feedback to the user when the PTD 100 recognizes that the user is in the target position. The haptic feedback can be used to alert the user that the user needs to change positions from the target position. In one embodiment, an electronic feedback module that is configured to provide electrical stimulation to the user in response to control signals from the microcontroller can be used instead of haptic feedback in order to influence the sleep position of the user. In one embodiment, an audio emitter can used as an alternative to or in addition to haptic feedback to influence sleep position.

According to an embodiment, in order to improve the ease of use of PTD 100, audiovisual output module 120 can be used as a means to communicate with the user. In one embodiment, voice messages can be provided via an audio circuit or speaker to provide feedback to user. For example, a voice message might be provided to indicate that the PTD 100 has slipped out of position or has fallen off. In another example, a voice message might be provided to indicate that the battery 155 is low or that the PTD 100 is running out of memory for storing data. One skilled in the art will recognize that other types of audio messages can be provided to user of the device to facilitate use of the device. In an alternative embodiment, an audio emitter can be used to project audio patterns that the user can be trained to recognize. For example, the audio emitter could be configured to emit a specific signal if the device is turned on or if the device has fallen off.

According to another embodiment, a light emitting diode (LED) can be used to identify when the PTD 100 is powered on, when the battery 155 is being charged, or alternatively when the battery 155 needs to be recharged, or when data is available for transfer from the PTD 100 or when data is being transferred from the PTD 100. In another embodiment, a display can be provided for displaying text messages, icons, or other visual indicators to the user regarding the operation of usages of the device. For example, the PTD 100 can include a liquid crystal (LCD) display, an LED display, or an organic light emitting diode (OLED) display for displaying information to the user of the device. One skilled in the art will recognize that microcontroller and firmware provides the means to apply any number of notifications or feedback using various combinations audio and visual feedback.

According to an embodiment, the PTD 100 can comprise low profile chips to minimize the profile of the PTD 100. For example, low profile chips can be used to implement microcontroller 130, position detector 110 (e.g., an accelerometer). In one embodiment, microcontroller 130, flash memory for data storage 170, and a USB chip for data transfer interface 175 can be mounted on a printed circuit board (PCB), and a triple-axis accelerometer for position detector 110 can be centered on the top of the PCB. Connectors for battery 155, haptic motor 140, a mini-USB connector for data transfer interface 175, light emitting diodes for audiovisual output module 120, and an on-off switch can be mounted on the bottom of the PCB. Passive components can be mounted in the available space around these components.

According to an embodiment, the on-off switch can be located where the user can readily switch on the PTD 100, but the switch can be sufficiently recessed so that the device cannot easily be inadvertently turned off during use (e.g., by catching the switch on bedding or a pillow or the user's head or body). Because the haptic motor utilizes can use a substantial amount of current, the number of nights of use for a given size battery prior to recharging can depend on how often the haptic motor is used to provide feedback to the user. In a preferred embodiment, haptic motor 140 is physically located within the enclosure of the PTD 100 such that the haptic motor 140 can transmit a maximum level of vibration with a minimal amount of power consumption.

Figure 2:
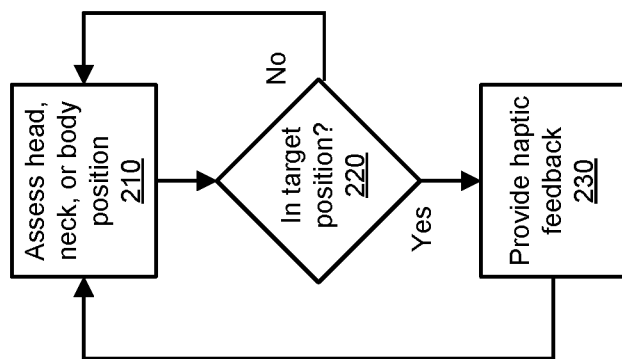
FIG. 2 is a flow diagram of a basic approach to reduce sleep in a target position using a the position therapy device illustrated in FIG. 1 to provide haptic feedback to induce a user to change sleep positions according to an embodiment.

FIG. 2 is a flow diagram of a method for using the PTD 100 to monitor and control the sleep position of a user according to an embodiment. As described above, the PTD 100 can be self-applied by a user and can be positioned on the head, neck, or body and is worn by the user during sleep.

Once the PTD 100 has been applied by the user, the PTD 100 can use a set of algorithms included in the firmware executed by microcontroller 130 to assess data collected by the position detector 110 to assess the sleeping position of the user (step 210). According to an embodiment, the position detector 110 comprises one or more accelerometers that can be used to assess the sleep position of the user. The PTD 100 monitors data received from the position detector 110 in order to make real-time assessments of the sleep position of the user. As described above, the PTD 100 can also include a microphone 105 that can be used to capture audio signals indicative of whether the user is snoring. In an embodiment, the audio data captured by microphone 105 can be analyzed by the firmware to determine whether the user is snoring, and the microcontroller 130 can write the data to data storage 170. In one embodiment, the audio data captured by the microcontroller 130 can be written to the data storage 170 and the stored audio data can be transferred from the PTD 100 to an external computer system for further analysis and processing. In some embodiments, the microcontroller 130 can be configured to execute one or more analysis algorithms implemented in the firmware on the data received from the microphone 105 to identify whether the user of the device is snoring. The microcontroller 130 can also be configured to write snoring event data to the data storage 170, and the stored snoring event data can later be transferred to an external computer system or web portal for further analysis and processing.

A determination is made whether a target sleep position is detected based on the assessment of the data from the position detector 110 (step 220). The target sleep position is a sleep position to be avoided. For example, the target sleep position for a patient with OSA may be a supine position, because sleeping on the back can cause the airway to be susceptible to collapse and can lead to inspiratory flow limitation. If the target position is the supine position and the PTD 100 determines that the user is sleeping in the target position, the PTD 100 can provide haptic feedback to the user (step 230) to influence the user's sleep position. For example, if the user is sleeping in a supine position and the target position is the supine position, haptic feedback can be provided to encourage the user to change position. According to an embodiment, haptic feedback can be elicited until the PTD 100 detects that the user h as changed position.

According to an embodiment, the PTD 100 can be worn for multiple nights between battery charges and over the course of the multiple nights, the PTD 100 can monitor compliance, the impact of the feedback on sleep continuity, behavioral arousals and sleep efficacy, and snoring.

According to an embodiment, the method illustrated in FIG. 2 can be adapted for use with users who are using the PTD 100 while awake. For example, the PTD 100 can be used to assess the position of the user (step 210) who is awake and to determine whether the user is in a target position (step 220) and provide haptic feedback to the user (step 230). For example, the PTD 100 could be used by a pregnant user to warn the user to avoid lying down in a supine position. In another example, the PTD 100 could be used to warn a patient with an arm or shoulder injury from lying on the injured side of the body.

Alternatively, the PTD 100 can be used to assist a person locate or avoid the appropriate position. For example, the precise position of the head, neck body or torso may be important for use in the rehabilitation of in injury. Haptic feedback can be used for positive reinforcement when a particular position is achieved, or for negative reinforcement, as described previously to avoid a particular position.

Figure 9:
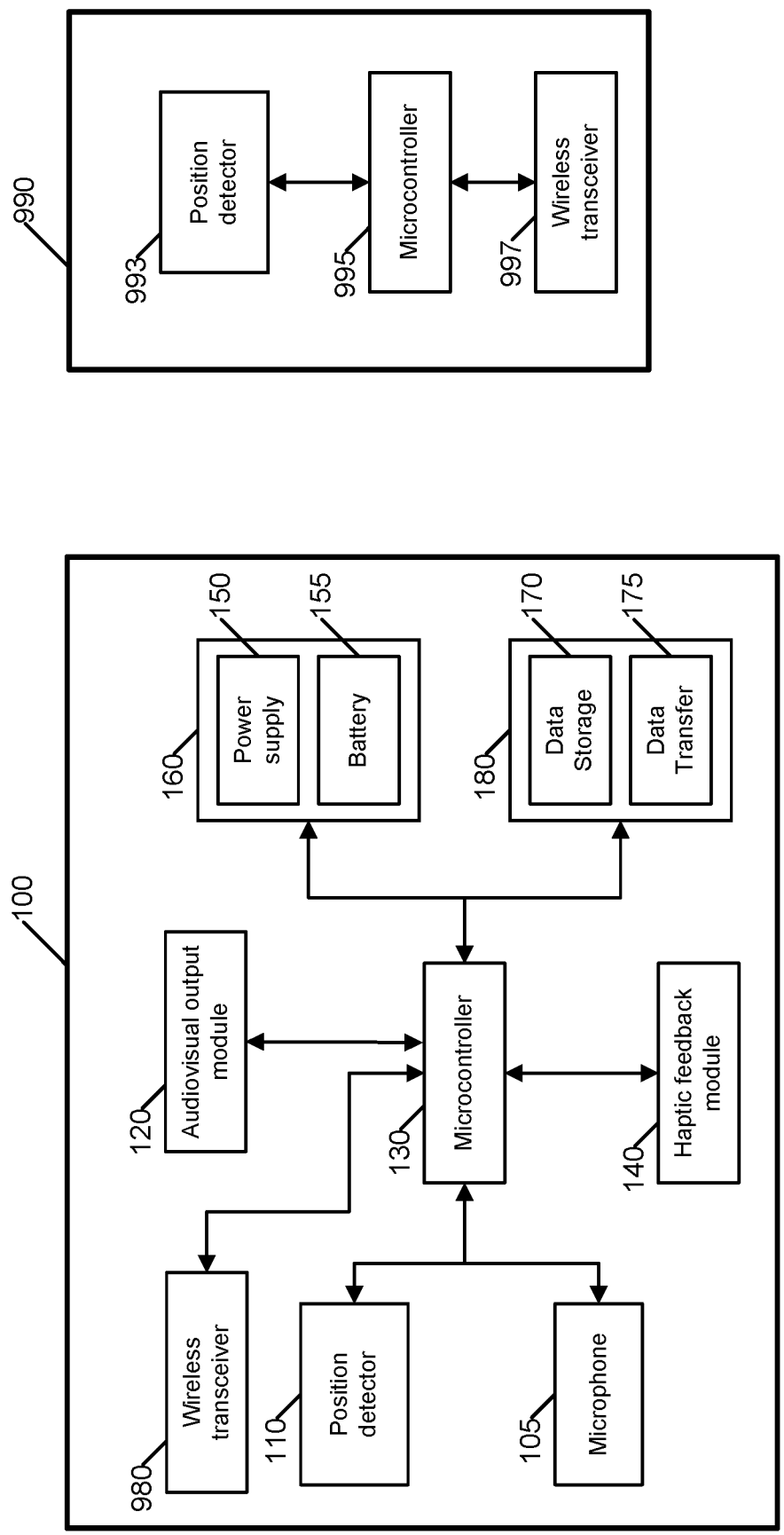
FIG. 9 illustrates an alternative embodiment of the position therapy device illustrated in FIG. 1 that includes a wireless transceiver.

FIG. 9 illustrates an alternative embodiment of the position therapy device illustrated in FIG. 1 that includes a wireless transceiver. The wireless embodiment of the PTD 100 illustrated in FIG. 9 can be used with any of various methods described herein in which the non-wireless version of the PTD 100 can be used. The embodiment of PTD 100 illustrated in FIG. 9 can remotely monitor the position of the user's body and provide haptic feedback to the user. The components of the PTD 100 illustrated in FIG. 9 are similar to those of FIG. 1, but the embodiment illustrated in FIG. 9 includes a wireless transceiver 980 that can be configured to allow the PTD 100 to communicate with one more remote position sensors 990. According to an embodiment, the wireless transceiver can be a Bluetooth transceiver, a Zigbee transceiver, or other type of wireless transceiver that can provide wireless communications between the PTD 100 and the remote position sensor 990. FIG. 9 illustrates the various components of the PTD 100 as being in communication with one another. The components can be in communication with one another via a wired or wireless connection.

The remote position sensor 990 includes a microcontroller 995, a position sensor 993, and a wireless transceiver 997. In an embodiment, the microcontroller 995 can be similar to microcontroller 130 of PTD 100 or can be of a different configuration. Position detector 993 can also be of a similar configuration as position detector 110 of PTD 100 or can be of a different configuration. In an embodiment, the PTD 100 can also include the wireless position detector 110 when the remote position sensor 990 is used, while in other embodiments, the PTD 100 can be configured to not include a wireless position sensor 110 when one or more wireless position sensors 990 are used.

Information collected by the remote position sensor 990 can be transmitted to the PTD 100. The microcontroller 130 can use this information to determine whether to generate a control signal to provide haptic feedback to the user with haptic feedback module 140.

In an embodiment, the remote sensor 990 can include a power supply 150, battery 155, and recharging circuit 160 similar to that of PTD 100. In other embodiments, the remote sensor 990 can include a non-rechargeable, replaceable battery to provide power to the remote sensor.

In one embodiment, more than one remote position sensors 990 can be used to provide information relating a position or positions of the head, torso, or extremities of a user. One skilled in the art will recognize the potential benefit of an athlete having multiple remote position sensors attached to key aspects of his body to ensure complex positions are maintained prior to execution of an action (e.g., preparing to hit a baseball, drive or put a golf ball, shoot a free throw, etc.). This approach allows for position information obtained during performance modeling, video taping, etc. to be translated to positions or angles of the body or extremities and in which haptic feedback can be used to assist the user to achieve that exact position (or similar position) during practice without access to the more sophisticated measurement approaches. In one embodiment the one or more remote sensors can be attached or woven into clothing, a glove(s), wristbands, socks, etc. to allow more accurate placement of the sensor relative to a part of the user's body. In one embodiment, multiple remote sensors 990 can be attached or incorporated into a garment or accessory, allowing more than one sensor to share use the same battery and/or transceiver. In one embodiment, an energy-harvesting module can be used to provide power to the battery of the remote sensor 990 and/or the PTD 100. The energy-harvesting module can generate power based on movements of the user during the use of the PTD 100.

In an alternative embodiment, the remote sensor 990 can be connected to the PTD 100 using a wired interface, and the PTD 100 and the remote sensor 990 can include appropriate physical interfaces for the wired connection. For example, in an embodiment, the remote sensor 990 and the PTD 100 can include data ports into which a data cable can be plugged to provide a wired communication connection between the remote sensor 990 and the PTD 100.

Figure 3:
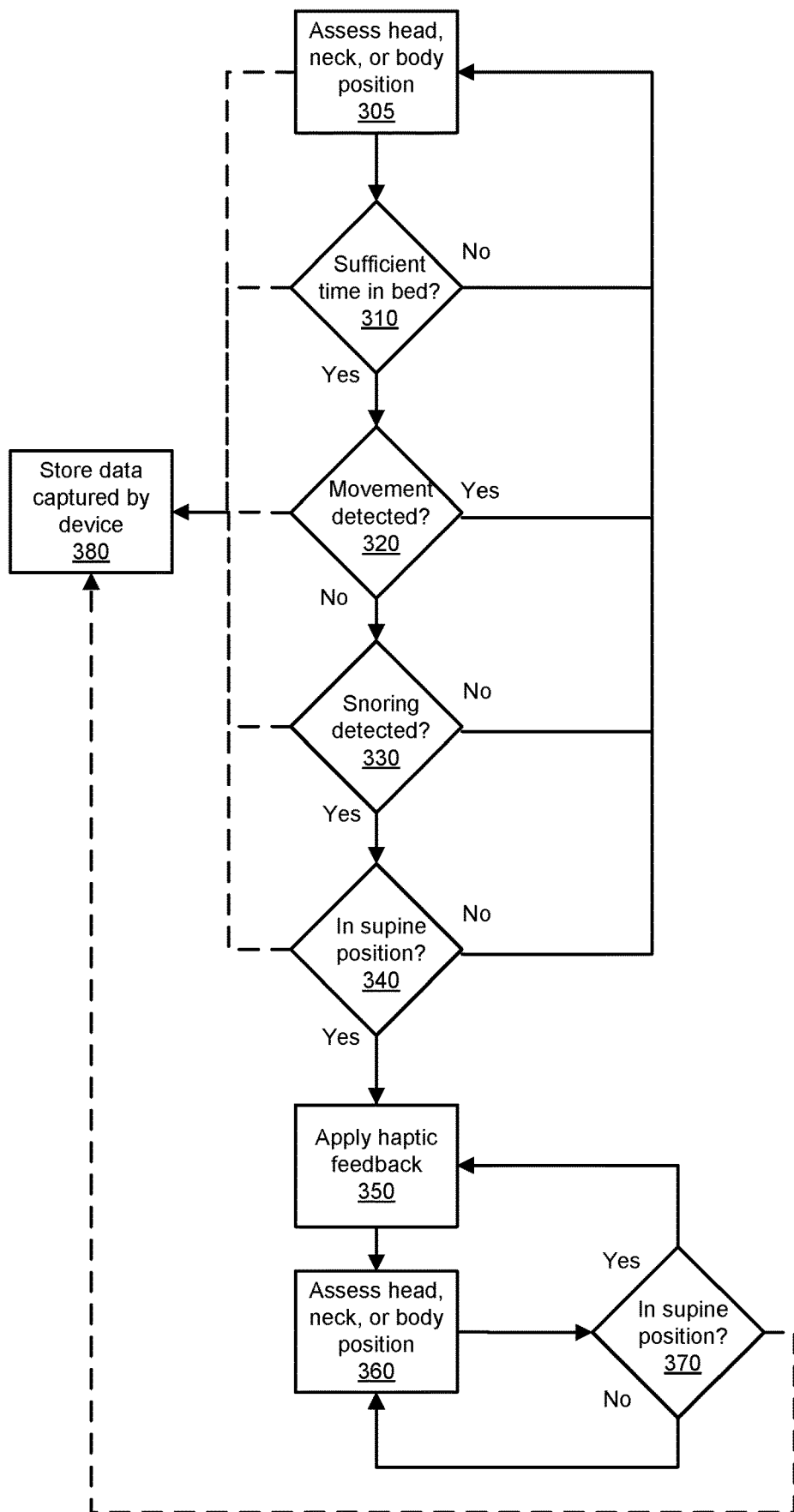
FIG. 3 illustrates another method for monitoring and influencing the sleep position using the position therapy device of FIG. 1 to provide haptic feedback to induce a user to change sleep positions according to an embodiment.

FIG. 3 illustrates another method for monitoring and influencing the sleep position of PTD 100 using conditional positional feedback according to an embodiment. The method illustrated in FIG. 3 is similar to that of FIG. 2, but the method illustrated in FIG. 3 is adapted to assist sleepers that have difficulty falling asleep in a position other than the target position. For example, the method illustrated in FIG. 3 can be used to assist predominantly supine sleepers that may have difficulty falling asleep on their sides by allowing the user to initially fall asleep in a supine position. The method provides the patient with an opportunity to fall asleep before using conditional feedback to influence the sleep position of the patient. This approach avoids compromising the sleep efficiency of the user by forcing the user to attempt to fall asleep in a non-target position when the user is typically unable to fall asleep in a non-target position. For example, if a user who is typically a supine sleeper will not be forced to attempt to fall asleep on her side.

As described above, the PTD 100 can be self-applied by a user and can be positioned on the head, neck, or body and is worn by the user during sleep. Once the PTD 100 has been applied by the user, the PTD 100 can use a set of algorithms included in the firmware executed by microcontroller 130 to assess data collected by the position detector 110 to assess the sleeping position of the user (step 305). A determination can then be made whether the user has had a sufficient amount of time in bed to make an assessment (step 310). In one embodiment positional feedback will be initiated only after a predetermined or configurable elapsed time period with the PTD 100 on (e.g., 15-minutes). For example, in some embodiments, the user and/or a doctor or therapist treating the patient can configure the amount of time that PTD 100 will wait before making an initial assessment, while in other embodiments, the PTD 100 can be configured to wait for a predetermined time period before making an initial assessment. If the user has not had a sufficient amount of time in bed prior to making an assessment, the method returns to step 305 where a new assessment can be made.

Otherwise, if the predetermined or configurable time period has elapsed a determination can be made whether movement is detected (step 320). For example, the user is moving his or her head or other parts of the body, then the user may still be awake. If movement is detected, the user is likely not to be asleep and positional feedback would not be effective. Therefore, the method returns to step 305 where a new assessment can be made.

According to an embodiment, a user can reset the time period on the PTD 100 if the user has trouble falling asleep. For example, a user might be awakened during the night by the need to use the bathroom, and upon returning from the nocturnal use of the bathroom, the user can turn the PTD 100 off and then back on in order to reset the feedback delay. According to an embodiment, the microcontroller 130 can include a real-time clock that can be used to timestamp the on/off mark in the data captured by the PTD 100 so that the data can be appended into a single of information when a compliance and efficacy report is generated from the data.

Otherwise, if no movement is detected, then the user is more likely to be asleep, and a determination can be made whether snoring is detected (step 330). As described above, the PTD 100 can include a microphone 105 that can be used to capture an audio signal that can be analyzed to determine whether the user is snoring. While lack of snoring is not indicative of whether the user is asleep, snoring is indicative that the user is asleep and can also be indicative of an airway susceptible to collapse and can lead to inspiratory flow limitation. If no snoring is detected, the user may not be sleeping, and thus positional feedback could be counterproductive. If the user is asleep and is not snoring, the user is likely to be in a non-target position (in this example, a non-supine position), and applying positional feedback might simply wake the user. Otherwise, if the user is not asleep, applying positional feedback could prevent the user from falling asleep. Therefore, the method returns to step 305 where a new assessment can be made.

According to an embodiment, step 330 can be optional if the user has satisfied the conditions of steps 310 and 320 and has been in bed for a sufficient amount of time and no movement has been detected. In some embodiments, the PTD 100 can be configured to track how much time has passed since the movement was detected in step 320, and if a predetermined period of time has passed since the last movement was detected, the method can proceed to step 340 even if no snoring is detected. For example, in one embodiment, if the user has been in bed for at least 15 minutes, the condition of step 310 is satisfied. No movement is detected at step 320 so the step is also satisfied, but if no snoring is detected, the method would return to step 305 even thought the user might be asleep. Therefore, the PTD 100 can begin keeping track of how long it has been since movement was last detected (or when step 320 was first performed if no movement has been detected since the method began), and if a predetermined time period (e.g., five minutes) passes an no movement is detected and no snoring is present, the method can proceed to step 340, because it is likely that the user is asleep but is not snoring.

Furthermore, in an alternative embodiment, if snoring is detected even if some movement is present, the snoring is indicative that the user is asleep, and the method can proceed to step 340. In yet another embodiment, the order of steps 320 and 330 can be reversed, so that the PTD 100 is configured to check for snoring before checking for user movements.

A determination can be made whether the user is in a supine position for embodiments where the target position is a supine position (step 340). According to an embodiment, a determination could be made whether the user is in other non-supine target positions depending upon the individual needs of the user and the condition for which the user is being treated. If the user is in the target position, haptic feedback can be provided to the user (step 350). In a preferred embodiment, once the user is asleep, feedback is provided immediately after a position change so as to not alter or disrupt the continuity of sleep more than what would normally occur when a sleeper changes position. In an embodiment, the position detector 110 can be used to detect that the user has changed position. For example, in one embodiment, the position detector 110 comprises one or more accelerometers that can be used to determine that the user's body position.

In one embodiment, the feedback stimulation routine begins at a low intensity level two-second haptic feedback interval when the supine position is detected. After applying the feedback to the user, an assessment can then be performed on data collected by the position detector 110 to assess the sleeping position of the user (step 360), and a determination can be made whether the user is in a supine position (step 370). According to an embodiment, if gross movement of the user's body position is not identified, an additional feedback routine sequence can be applied. For example, in an embodiment, if the PTD 100 does not detect that the patient has begun to change position within four seconds of the termination of the previous feedback routine, another 2 second long feedback routing can be presented at a higher intensity level than the previous feedback routine. According to an embodiment, the sequence of steps 350, 360, and 370 can be repeated until the user finally changes positions and settles into a non-supine position 370.

According to an embodiment, the PTD 100 can also be configured to store the data received from the position detector 110 and the microphone 105 (step 380). According to an embodiment, the data received by the microphone 105 can be analyzed by the PTD 100 to determine whether the user is snoring, and data indicating whether the user was snoring and a particular data and time can be stored in the data storage 170. According to an embodiment, other data can also be collected by the PTD 100 and stored in the data storage 170. For example, the PDT 100 can configured to determine a current sleep state of the user, a current sleep position of the user, feedback that was provided to the user, and/or other information that can be used to determine the quality of the user's sleep and the efficacy of the PTD treatment.

According to an embodiment, the final intensity of the haptic feedback provided to the user that resulted in the user changing position can be saved to data storage 170 and can be used as a starting level for the haptic feedback provided the next time that feedback is required. The patterns of haptic feedback described above are merely one example of the pattern of feedback that can be used to influence the sleeping of the user. In other embodiments, different patterns of haptic feedback including different haptic feedback intervals and lengths of pauses between intervals of increasing intensity of feedback can be used. According to an embodiment, a different number of haptic motors 140 can also be used to create a subjective perception of increased levels of feedback.

According to an embodiment, the firmware of PTD 100 can be configured to store data representing the average feedback intensity levels and range of feedback intensity levels required to initiate position changes. This data can be stored in data storage 170, and the PTD 100 can utilize this information the next time the PTD 100 is used to establish the initial feedback pattern. Thus, the patterns and intensity of the feedback can be tailored to the individual user in order to encourage positional behavior without over-stimulation. For example, by using the techniques described above, the PTD 100 will not stimulate a light sleeper fully awake, and the PTD 100 won't under stimulate a heavy sleeper, such that the feedback produced by the PTD 100 is ignored.

The feedback intensity is adaptive so that the therapy can also be efficacious in patients who are taking analgesic medications, sleeping pills, or consuming alcohol prior to bed. The conditional algorithms can accommodate changes in the user's sensitivity to the feedback based on sleep stage or adaptation to continued use of the PTD 100. PTD 100 can be configured to use various numbers of feedback intensity levels, as well as various lengths of the feedback and durations between feedback events without negatively impacting the functionality of the PTD 100.

According to an embodiment, the position detector 110 comprise accelerometers that are sensitive enough provide data that can be used to monitor the breathing of the user. The breathing pattern of the user can be collected as part of the position therapy data collected by the PTD 100 and can be used to identify interruptions and arousals in the sleep pattern of the user. For example, in an OSA patient, the patient's breathing can be interrupted resulting in the patient gasping for air. The data collected by the accelerometers can be analyzed to identify such events. The breathing data collected by the PTD 100 can also be used in determining whether the user is asleep, and can in some embodiments, be used in addition to or instead of the detection of user movement in step 330. For example, the user's breathing pattern can change when the user falls asleep and this change in breathing pattern can be identified in real time by monitoring and analyzing the signal data from the accelerometer or accelerometers.

Figure 4:
FIG. 4 illustrates a method for processing and analyzing the data acquired by the position therapy device of FIG. 1 according to an embodiment.

FIG. 4 illustrates a method for processing the data acquired by the PTD 100. As described above with respect to FIGS. 2 and 3, the PTD 100 captures and stores data regarding the sleep state of the user (step 405). In one embodiment, this data can be stored in the data storage 170 of the PTD 100. The data acquired by the PTD 100 can be transferred to an external computer system or web portal (step 410) for additional processing to assess various parameters useful in assessing compliance and efficacy (step 420). According to one embodiment, the data can be transferred from the PTD 100 using the data transfer interface 175. As described above the data transfer interface 175 can comprise a USB interface for transferring the data acquired by the PTD 100 to an external computer system or a web portal.

The frequency of use of the PTD 100, based on hours per night and nights per week can provide useful measures for assessing the user's compliance with PTD therapy. Other data captured by the PTD 100, such as the response time to positional feedback and length of time, the number of times per night the patient attempts to sleep supine, the total and percentage of time the patients user supine, and whether the user turn the device off in the night to eliminate feedback can also provide useful measures of treatment efficacy. According to an embodiment, the positional signal data from position detector 110 of the can represent actigraphic data. Actigraphy is a non-invasive method for monitoring the rest and activity cycles of a patient. The PTD 100 can measure the motor activity of the user and this data can be captured and stored by the PTD 100 as part of the position therapy data. The motor activity data can be analyzed to measure the behavioral sleep patterns of the user and sleep efficiency. This data can be incorporated into a position therapy report generated for the user. In some embodiments, night to night differences in the amplitude and frequency of snoring are additional measures which can also incorporated into a position therapy report to assist the user or their clinician assess the benefits of the PTD 100.

Figure 8:
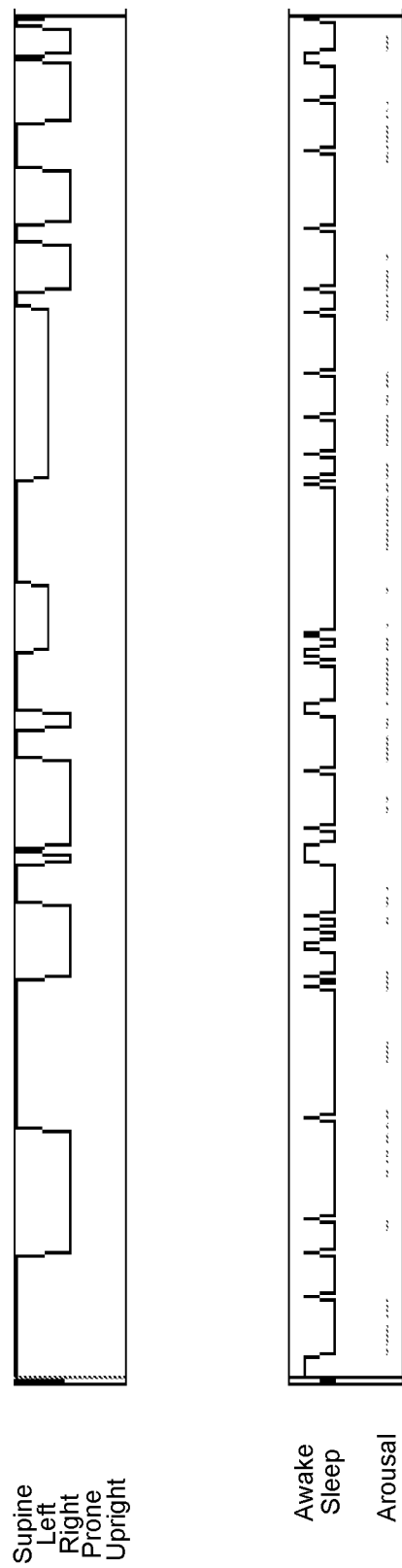
FIG. 8 uses a sample hypnogram to illustrate the clinical information that can be derived from accelerometers with the position therapy device and can be included in a position therapy report generated from data collected by the position therapy device according to an embodiment.

The external computer system or web portal can generate a report based on the position therapy data collected and/or generated by the PTD 100. The position therapy report position therapy report can assist the user or a clinician to assess the benefits of the positional therapy regime. Once the report has been generated, the report can be downloaded or printed (step 440) or viewed online. FIG. 8 is an example of a report that can be generated using the data captured by the PTD 100. The example report includes two graphs of data captured by the user device over time. The upper graph portion of the report includes positional data indicating the body position of the user over time. The lower graph illustrates the whether the user was awake or asleep over time and whether the user experienced an arousal event. This report can be downloaded for review by the patient or a clinician to assess the efficacy of the PTD therapy.

According to an embodiment, the PTD 100 can be interfaced with an external computer system or web portal to provide additional capabilities for monitoring treatment efficacy. For example, the PTD 100 can be configured to record sleep position of the user without applying feedback for a predetermined number period of time, such as one or more nights, to create baseline information about the user's preference for sleeping positions and other sleeping habits. Once the baseline data has been recorded, positional feedback can be initiated. The baseline data can later be compared to data collected after positional feedback has been initiated to determine whether the positional therapy is having an affect on the user's sleep habits.

In some embodiments, the PTD 100 can be configured via a user interface provided by the external computer system or web portal. For example, in some embodiments, the user interface is configured to allow the user to select a sleep position that the user wishes to avoid. In an example, the user might configure the PTD 100 to avoid the supine position for OSA or for pregnancy, or non-supine sleep for patients with shoulder or arm injuries. According to an embodiment, the user interface can also be configured to allow the user or a clinician to configure other parameters affecting haptic feedback or the algorithms used to make the various determinations described used in the method described above, such as the date and time.

Figure 5:
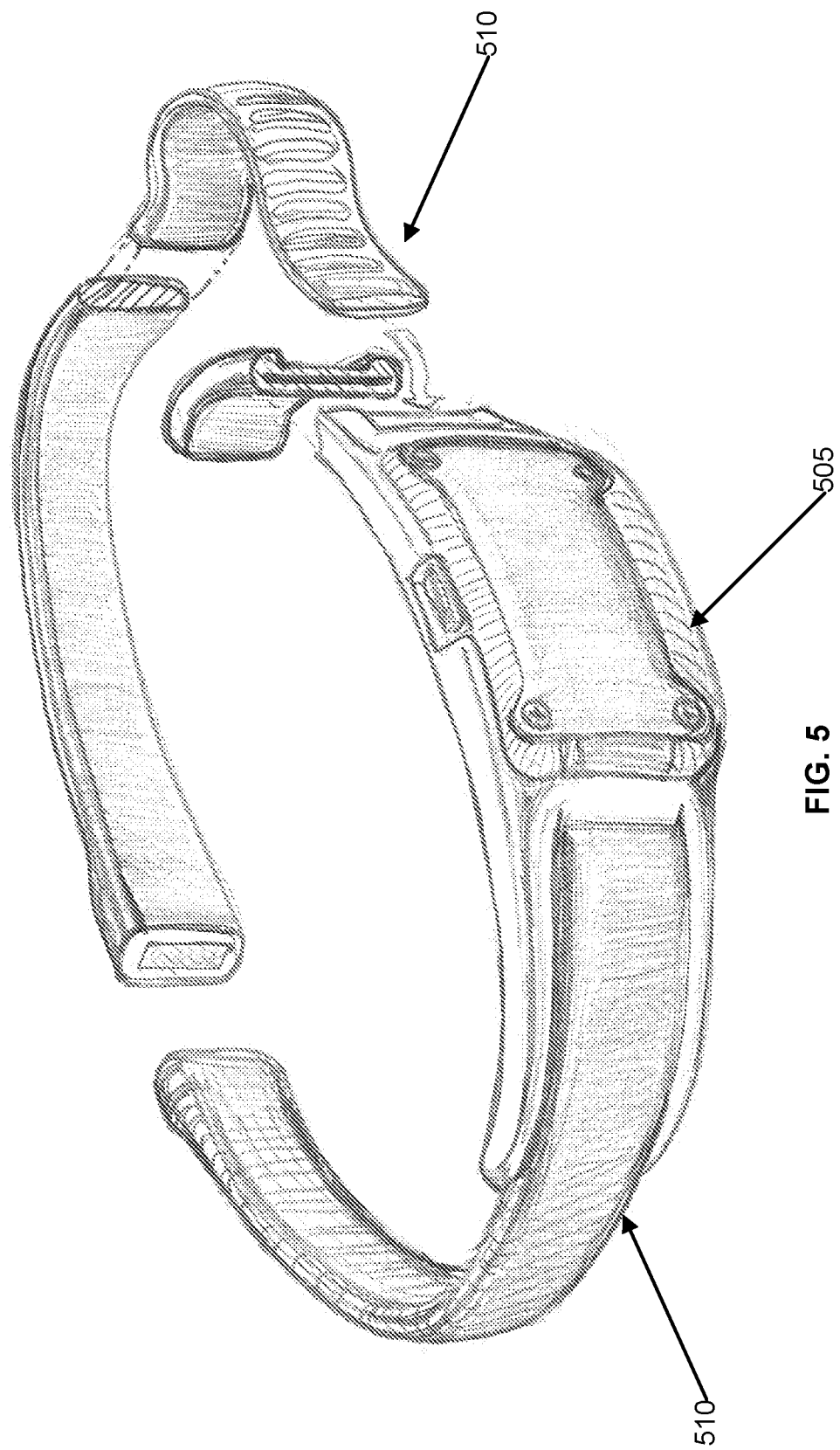
FIG. 5 provides an illustration of the position therapy device according to an embodiment.

FIG. 5 illustrates an example embodiment of the PTD 100. In the embodiment illustrated in FIG. 5, the PTD 100 comprises a small injection-molded silicon enclosure 505. The silicon enclosure 505 encapsulates the electronic components of the PTD 100 and the enclosure is thick enough to protect the electronic components. A thinner, more comfortable durometer silicone can be used for the enclosure extensions 510. In an embodiment, a thin strip of copper can be molded inside of the extensions to allow the PTD 100 to be adjusted to conform to the neck or back of the user and to decrease the likelihood that the PTD 100 might accidentally be repositioned during sleep and result in false positive feedback. The silicone enclosure 505 and enclosure extensions 510 can be easily cleaned and maintained with alcohol.

Figure 6:
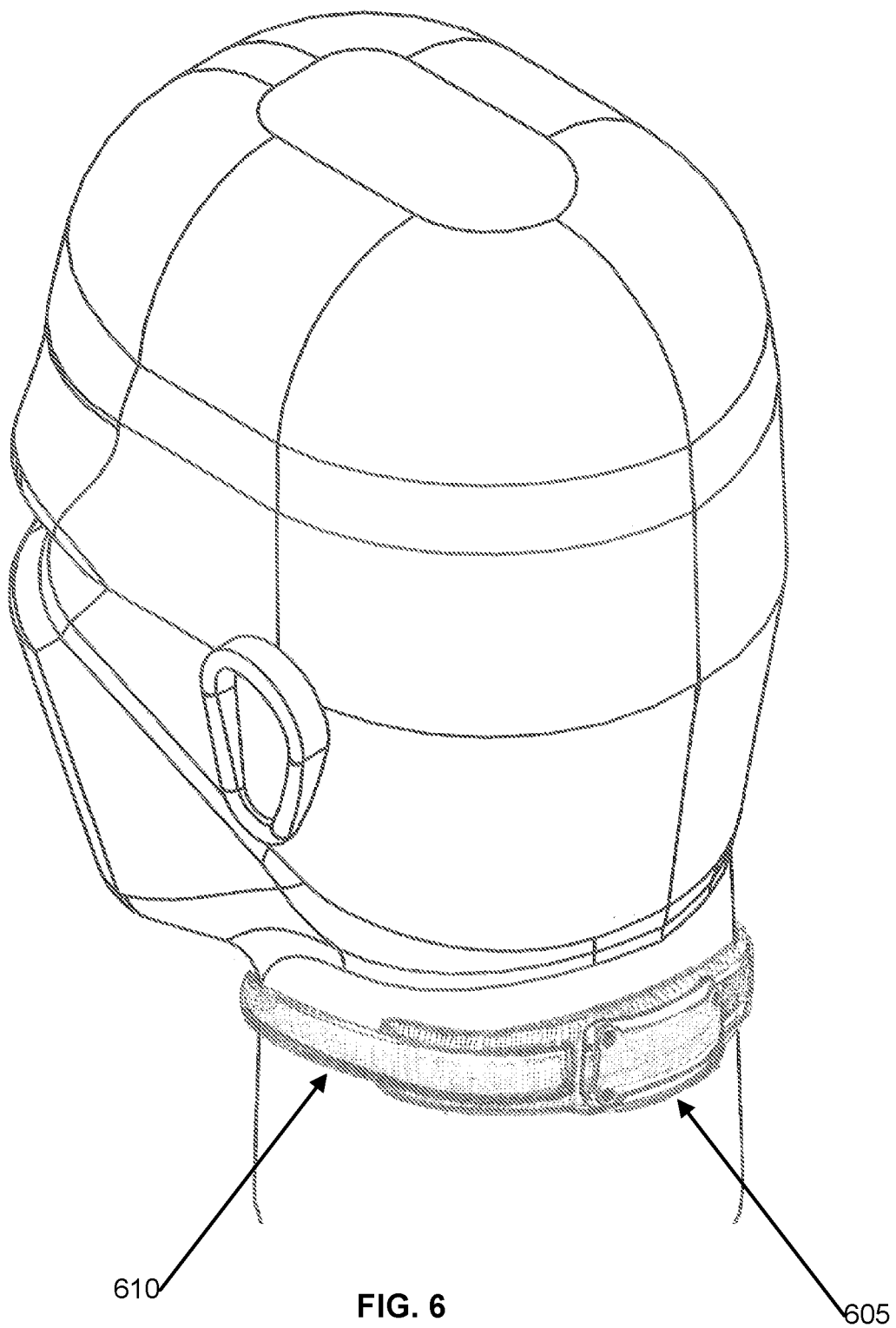
FIG. 6 shows the position therapy device worn around the neck according to an embodiment.

FIG. 6 illustrates the PTD 100 design illustrated in FIG. 5 that has been placed around the neck of a user according to an embodiment. In the embodiment illustrated in FIG. 6, a thin, round silicone enclosure strap 610 holds the enclosure 605 of the PTD 100 in place round the user's neck. The length of the left and right straps can be adjusted over the enclosure 605. According to an embodiment, a low profile magnetic clasp (not shown), similar to that used in some wrist bracelets, can be used on the front of the strap of the PTD 100 to allow the PTD 100 to be easily applied or taken off by the user. According to an embodiment, to cover safety concerns regarding wearing a collar during sleep, the strength of the magnet included in the magnetic clasp can be selected to ensure that the magnetic clasp will automatically release in the event that the PTD 100 were to get caught in the clothing of the user or the bedding.

Figure 7:
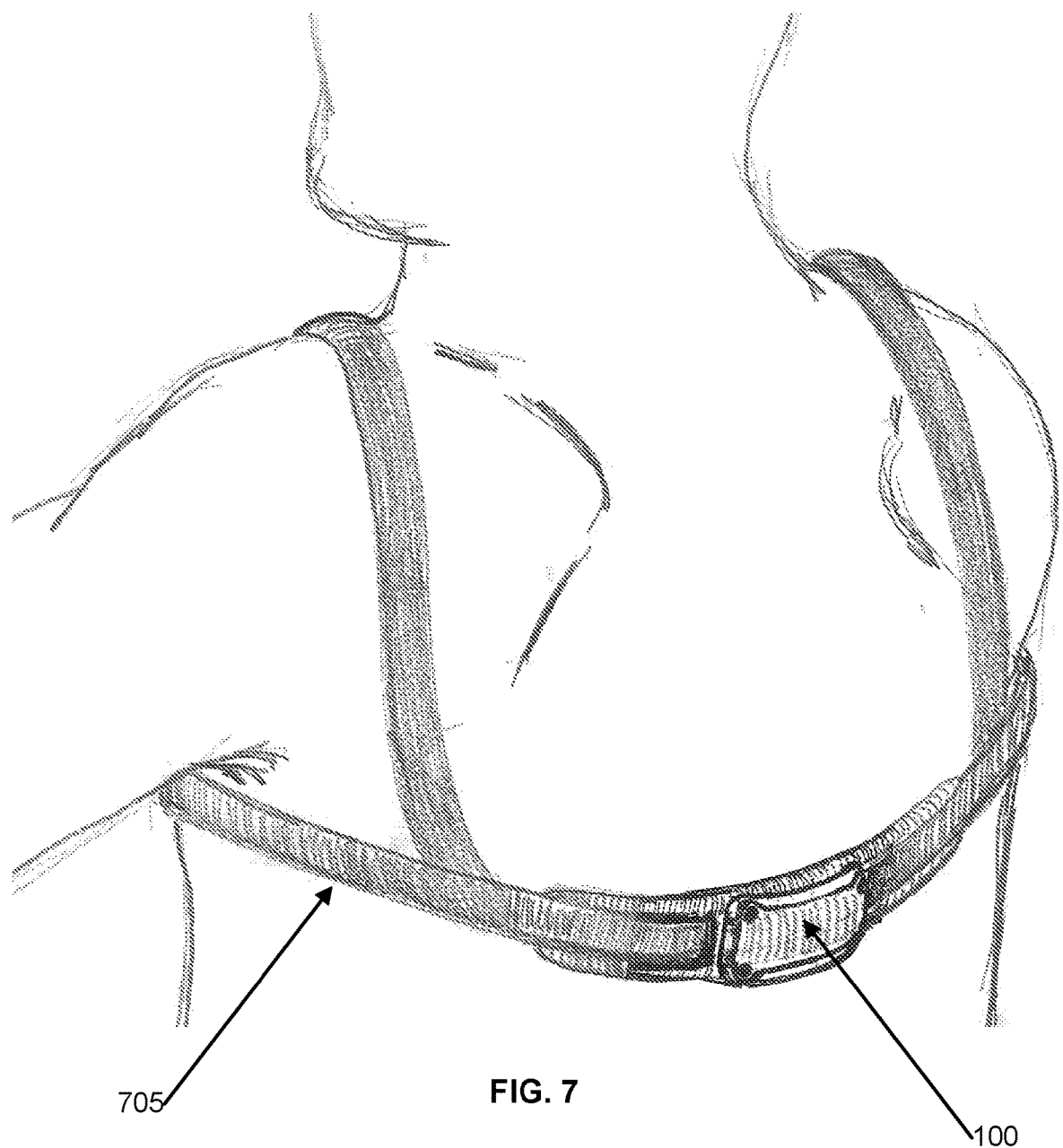
FIG. 7 shows the position therapy device worn on the back.

FIG. 7 illustrates another embodiment of the PTD illustrated in FIGS. 5 and 6 where the enclosure 705 can be worn over the spine and can be held in place with the use of a longer, thicker enclosure strap 705 than is used in the embodiments illustrated in FIGS. 5 and 6. The enclosure strap wraps around the chest and over the shoulders of the user to hold the PTD 100 in place.

Those of skill in the art will appreciate that the various illustrative modules and method steps described in connection with the above described figures and the embodiments disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for ease of description. Specific functions can be moved from one module or step to another without departing from the invention.

Moreover, the various illustrative modules and method steps described in connection with the embodiments disclosed herein can be implemented or performed with hardware such as a general purpose processor, a digital signal processor ("DSP"), an application specific integrated circuit ("ASIC"), field programmable gate array ("FPGA") or other programmable logic device, discrete gate or transistor logic, discrete hardware components, or any combination thereof designed to perform the functions described herein. A general-purpose processor is hardware and can be a microprocessor, but in the alternative, the processor can be any hardware processor or controller, microcontroller. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in computer or controller accessible on computer-readable storage media including RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent exemplary embodiments of the invention and are therefore representative of the subject matter which is broadly contemplated by the present invention. It is further understood that the scope of the present invention fully encompasses other embodiments and that the scope of the present invention is accordingly limited by nothing other than the appended claims.

What is claimed is:

1. A method for providing position feedback to a user, the method comprising:
receiving positional data from one or more position detectors of a wearable device while the user is wearing the wearable device;
based on the positional data, determining whether the user is in a target position or one or more non-target positions;
when it is determined that the user is in the target position, generating feedback by one or more feedback generators of the wearable device to influence the user to change to the one or more non-target positions; and generating a report of the position feedback based on time spent in the target position and one or more non-target positions.

2. The method of claim 1 further comprising providing an assessment of the efficacy of the position feedback based on the measure of time spent in the target and one or more non-target positions over a time period.

3. The method of claim 1 wherein the determining whether the user is in the target position or one or more non-target positions is determined over a time period.

4. The method of claim 1, further comprising delaying the feedback for at least a predetermined or configurable time period.

5. The method of claim 1, wherein the generating a report of the position feedback is based on the wearable device being worn on one of the body head and neck.

6. The method of claim 1, wherein the generating a report of the position feedback is based on at least one additional measure comprising one or more of:
- a number of changes in position that occur during use of the wearable device,
- a total amount of time that the wearable device is used,
- interruptions in sleep that occur during use of the wearable device,
- a measure of movements that occur during use of the wearable device,
- an amount of feedback that was provided to the user by the wearable device,
- a length of feedback delivered during use of the wearable device,
- the user's response time to the feedback,
- a number of times that the user is in the target position, and
- efficacy based on one of a total time the user spends in the target position and a percentage of time spent in the target position.

7. The method of claim 6, wherein, when the at least one additional measure comprises interruptions in sleep, the method further comprises determining the interruptions in sleep based on changes in position.

8. The method of claim 1, further comprising the wearable device collecting the breathing pattern of the user, wherein the generating a report of the position feedback is based on at least one additional measure comprising interruptions in sleep which are determined based on the collected breathing pattern of the user.

9. The method of claim 1, further comprising capturing audio data and wherein the generating a report of the position feedback is based on at least one additional measure comprising a snoring frequency.

10. The method of claim 9, wherein the report is based on a relationship between one of snoring frequency and snoring magnitude during the time spent in the target and non-target positions.

11. The method of claim 1, further comprising, by the wearable device, transmitting information to an external system which providing an assessment of the efficacy of the position feedback based on the time spent in the target and non-target positions, wherein the time spent in the target and non-target positions is derived from the transmitted information.

12. The method of claim 1, wherein generating the report of the position feedback comprises, by the wearable device, collecting positional data, without applying feedback, to generate baseline data, wherein the report of the position feedback is based on a comparison to the baseline data.

13. The method of claim 12, wherein the comparison to the baseline data comprises determining a difference between an amount of time spent in the target position, with application of the feedback, and an amount of time spent in the target position, without application of the feedback.

14. The method of claim 12, wherein the comparison to the baseline data comprises determining a difference between a number of attempts to be in the target position, with application of the feedback, and a number of attempts to be in the target position, without application of the feedback.

15. The method of claim 1, wherein providing feedback comprises adaptively increasing the feedback until the user changes to the non-target position.

16. The method of claim 15, wherein increasing the feedback comprises one or more of increasing an intensity of the feedback, increasing a length of the feedback, and decreasing a duration between feedback events.

17. A device wearable by a user, the device comprising:
- at least one position detector which generates positional data of the user while the user is wearing the device;
- at least one feedback generator which generates feedback; and
- at least one processor communicatively coupled to the at least one position detector and the at least one feedback generator, the at least one processor configured to execute instructions stored in a memory to provide position feedback to the user wearing the device by:
  - receiving positional data from the at least one position detector while the user is wearing the device,
  - based on the positional data, determining whether the user is in a target position or one or more non-target positions,
  - when it is determined that the user is in the target position, generating feedback by the at least one feedback generator of the wearable device to influence the user to change to the one or more non-target positions, and
  - generating a report of the position feedback based on time spent in the target position and one or more non-target positions.

18. A wearable device for providing position feedback to a user while the device is worn by the user, the device comprising:
- one or more position detectors which generate positional data of the user while the user is wearing the device;
- one or more feedback generators which generate feedback; and
- at least one processor communicatively coupled to the one or more position detectors and the one or more feedback generators, the at least one processor configured to execute instructions stored in a memory to influence the user to change position from a target position to one or more non-target positions by:
  - collecting positional data via the one or more position detectors while the user is wearing the wearable device,
  - based on the positional data, determining whether the user is in the target position or one or more non-target positions, and
  - when it is determined that the user is in the target position, adaptively delivering feedback by increasing the feedback generated by the one or more feedback generators until the user changes to the one or more non-target positions.

19. The wearable device of claim 18, wherein the at least one processor is further configured to generate a report based on time spent in the target position and one or more non-target positions.

20. The wearable device of claim 18, wherein increasing the feedback comprises one or more of increasing a number of feedback generators used after each of one or more time intervals, increasing an intensity of the generated feedback, increasing a length of the generated feedback, and decreasing duration between generated feedback events.

\* \* \* \* \*